US012797020B2

(12) United States Patent
Nakai

(10) Patent No.: US 12,797,020 B2
(45) Date of Patent: Nov. 17, 2026

(54) COMPRESSION PLATE FOR MEDICAL IMAGING APPARATUS, POLYMETHYLPENTENE RESIN-CONTAINING MATERIAL, AND MEDICAL IMAGING APPARATUS

(71) Applicant: FUJIFILM Corporation, Tokyo (JP)

(72) Inventor: Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 18/790,634

(22) Filed: Jul. 31, 2024

(65) Prior Publication Data

US 2024/0389958 A1 Nov. 28, 2024

Related U.S. Application Data

(63) Continuation of application No. PCT/JP2023/010160, filed on Mar. 15, 2023.

(30) Foreign Application Priority Data

Mar. 30, 2022 (JP) ................................ 2022-056276

(51) Int. Cl.
*A61B 6/04* (2006.01)
*A61B 6/00* (2024.01)
(Continued)

(52) U.S. Cl.
CPC .......... *A61B 6/0414* (2013.01); *A61B 6/4417* (2013.01); *A61B 8/403* (2013.01);
(Continued)

(58) Field of Classification Search
None
See application file for complete search history.

(56) References Cited

U.S. PATENT DOCUMENTS 4,699,150 A 10/1987 Kawabuchi et al.
5,922,812 A * 7/1999 Kan ........................ C08L 23/20 525/240
(Continued)

FOREIGN PATENT DOCUMENTS

JP 59-225044 A 12/1984
JP 61-110049 A 5/1986
(Continued)

OTHER PUBLICATIONS

TPX RT18—Mitsui Chemicals America—Prospector (Dec. 21, 2020) (Year: 2020).*
(Continued)

*Primary Examiner* — Vivian Chen
(74) *Attorney, Agent, or Firm* — Sughrue Mion, PLLC

(57) ABSTRACT

There are provided: a compression plate for a medical imaging apparatus, which is used in a medical imaging apparatus including a radiation generation unit, a radiation detection unit, an ultrasound probe, and an imaging table disposed between the radiation generation unit and the radiation detection unit and which is used for compressing a subject by sandwiching the subject between the imaging table and the compression plate, the compression plate for a medical imaging apparatus including a polymethylpentene resin-containing material having a bending elastic modulus of 1 GPa or more and a thermal deformation temperature of 100° C. or higher, in which the polymethylpentene resin-containing material contains a polymethylpentene compound containing 1 to 300 ppm of a sulfur element based on mass; a polymethylpentene resin-containing material that is suitably used for the compression plate; and a medical imaging apparatus having the compression plate.

9 Claims, 1 Drawing Sheet

(51) Int. Cl.

| | |
|---|---|
| ***A61B 6/50*** | (2024.01) |
| ***A61B 8/00*** | (2006.01) |
| ***A61B 8/08*** | (2006.01) |
| ***C08F 10/14*** | (2006.01) |
| ***C08F 210/14*** | (2006.01) |
| ***C08L 23/04*** | (2006.01) |
| ***C08L 23/0807*** | (2025.01) |
| ***C08L 23/14*** | (2006.01) |
| ***C08L 23/16*** | (2006.01) |
| ***C08L 23/18*** | (2025.01) |
| ***C08L 23/20*** | (2025.01) |
| ***C08L 23/26*** | (2025.01) |

(52) U.S. Cl.

CPC ................. *A61B 6/502* (2013.01); *A61B 8/00* (2013.01); *A61B 8/0825* (2013.01); *C08F 10/14* (2013.01); *C08F 210/14* (2013.01); *C08L 23/04* (2013.01); *C08L 23/0807* (2013.01); *C08L 23/14* (2013.01); *C08L 23/16* (2013.01); *C08L 23/18* (2013.01); *C08L 23/20* (2013.01); *C08L 23/26* (2013.01)

(56) References Cited

U.S. PATENT DOCUMENTS

| | | | | |
|---|---|---|---|---|
| 2003/0149364 | A1 | 8/2003 | Kapur et al. | |
| 2012/0220728 | A1* | 8/2012 | Uekusa | C08L 23/20 525/240 |
| 2017/0281124 | A1* | 10/2017 | Arai | A61B 8/0825 |
| 2017/0298160 | A1* | 10/2017 | Uekusa | C08F 210/06 |
| 2018/0228464 | A1 | 8/2018 | Yang et al. | |
| 2019/0048109 | A1* | 2/2019 | Tanaka | B29C 48/00 |
| 2020/0305836 | A1 | 10/2020 | Arai et al. | |
| 2020/0390418 | A1 | 12/2020 | Fujimoto et al. | |
| 2021/0139622 | A1* | 5/2021 | Tanaka | C08L 23/20 |
| 2022/0048846 | A1 | 2/2022 | Iwasaki et al. | |

FOREIGN PATENT DOCUMENTS

| | | | |
|---|---|---|---|
| JP | 06-345916 | A | * 12/1994 |
| JP | 2009-82399 | A | 4/2009 |
| JP | 2010-252065 | A | 11/2010 |
| JP | 2014-233532 | A | 12/2014 |
| JP | 2018-62476 | A | 4/2018 |
| JP | 6598721 | B2 | 10/2019 |
| JP | 2020-162931 | A | 10/2020 |
| WO | 2020/054492 | A1 | 3/2020 |

OTHER PUBLICATIONS

"Investigation of Methylpentene Polymer (TPX) Molding Resin" (Mar. 1978) (Year: 1978).*

International Search Report dated May 23, 2023, issued in International Application No. PCT/JP2023/010160.

Written Opinion dated May 23, 2023, issued in International Application No. PCT/JP2023/010160.

International Preliminary Report on Patentability (with translation of Written Opinion) dated Sep. 24, 2024, issued in International Application No. PCT/JP2023/010160.

* cited by examiner

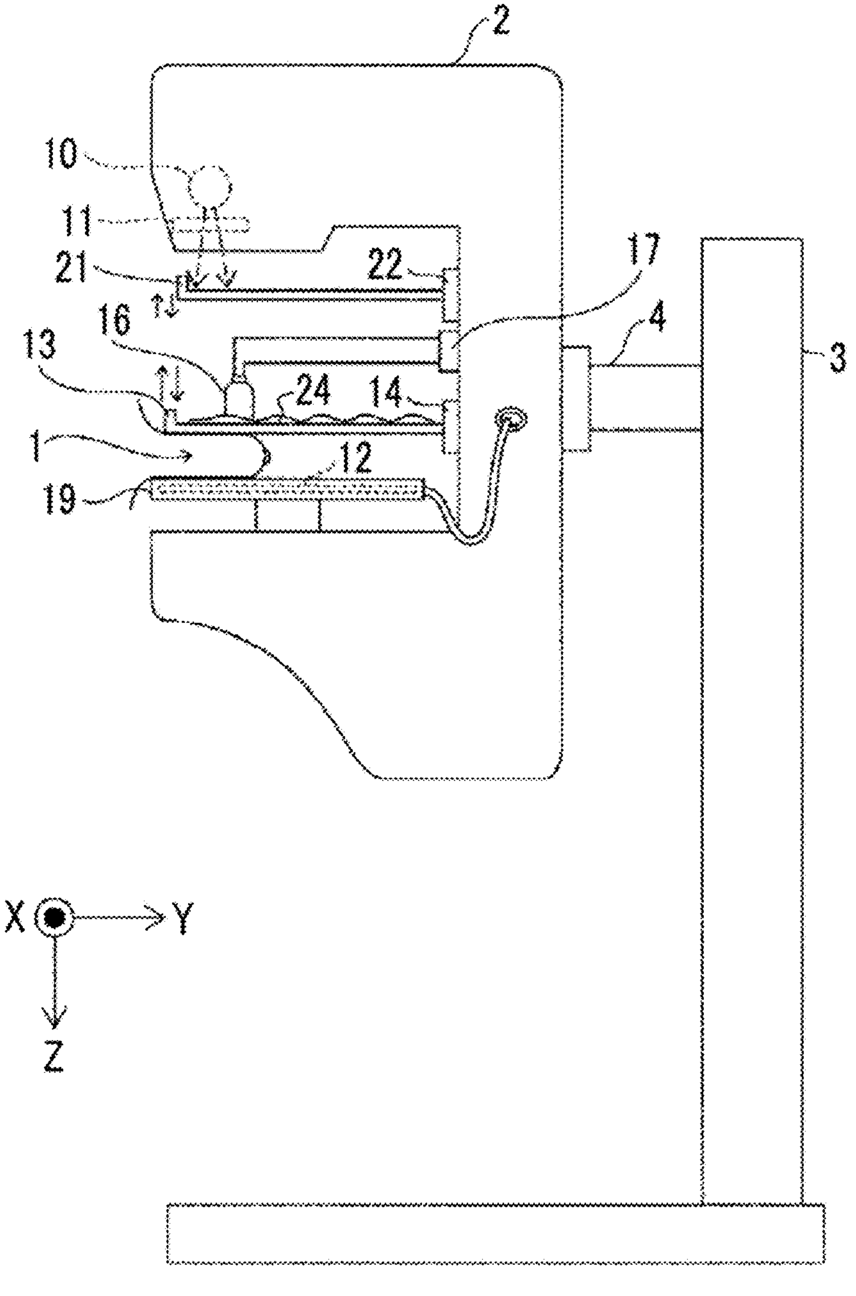
2
10
11
21
22
17
16
13
24
14
4
3
1
12
19
X
Y
Z

COMPRESSION PLATE FOR MEDICAL IMAGING APPARATUS, POLYMETHYLPENTENE RESIN-CONTAINING MATERIAL, AND MEDICAL IMAGING APPARATUS

CROSS-REFERENCE TO RELATED APPLICATIONS

This application is a Continuation of PCT International Application No. PCT/JP2023/010160 filed on Mar. 15, 2023, which claims priority under 35 U.S.C. § 119(a) to Japanese Patent Application No. 2022-056276 filed in Japan on Mar. 30, 2022. Each of the above applications is hereby expressly incorporated by reference, in its entirety, into the present application.

BACKGROUND OF THE INVENTION

1. Field of the Invention

The present invention relates to a compression plate for a medical imaging apparatus, a polymethylpentene resin-containing material, and a medical imaging apparatus.

2. Description of the Related Art

Imaging of a human body with radiation is one of the most important means for diagnosis. For example, breast cancer is diagnosed using an image obtained by imaging a breast with X-rays. However, since the image obtained using the X-rays obtains information on a three-dimensional subject (breast) as a two-dimensional image, there is a limitation to an accuracy of the diagnosis, such as not being able to grasp a position of a tumor in a depth direction even in a case in which the tumor is found.

As a technique for dealing with such a problem, there has been developed an imaging apparatus that combines radiation and an ultrasonic wave to obtain a two-dimensional image by the radiation and a three-dimensional image by the ultrasonic wave in one examination (for example, JP2009-82399A). The imaging apparatus disclosed in JP2009-82399A includes a first compression plate that compresses a subject between the imaging apparatus and an X-ray imaging table, an ultrasound probe that moves along an upper surface of the first compression plate on which echo jelly is applied and scans the subject with an ultrasonic wave to acquire an ultrasound image of the subject, and a second compression plate that compresses the echo jelly between the first compression plate and the second compression plate to make a thickness of the echo jelly uniform. JP2009-82399A discloses that resins such as polymethylpentene, polycarbonate, acrylic, or polyethylene terephthalate are used as a material of the first compression plate and the second compression plate, and among these resins, polymethylpentene has low rigidity and is suitable as a material of the first compression plate.

SUMMARY OF THE INVENTION

In a case in which the ultrasound probe repeatedly performs scanning along the compression plate over a long period of time and is pressed against or rubbed against the compression plate, stress and heat generated in a case in which the ultrasound probe emits an ultrasonic wave are repeatedly applied to the compression plate. As described above, polymethylpentene is suitable as a material for the compression plate from the viewpoint of rigidity and the like. However, the present inventor has conducted extensive studies on the compression plate consisting of polymethylpentene from the viewpoint of repeated use for a long period of time of the medical imaging apparatus, and has found that the repeated use for a long period of time of the medical imaging apparatus may cause the compression plate to be abraded or deformed, and a shift in focus of the obtained three-dimensional image may occur. In addition, it has been found that oxidative degradation of polymethylpentene itself may cause a shift in focus of the three-dimensional image or cause yellowing of the compression plate.

An object of the present invention is to provide a compression plate for a medical imaging apparatus that has excellent rigidity and is resistant to thermal deformation, abrasion, and yellowing, a polymethylpentene resin-containing material that is suitably used for the compression plate, and a medical imaging apparatus having the compression plate.

The above-mentioned object has been achieved by the following means.

<1>

A compression plate for a medical imaging apparatus, which is used in a medical imaging apparatus including a radiation generation unit, a radiation detection unit, an ultrasound probe, and an imaging table disposed between the radiation generation unit and the radiation detection unit and which is used for compressing a subject by sandwiching the subject between the imaging table and the compression plate, the compression plate for a medical imaging apparatus comprising:

- a polymethylpentene resin-containing material having a bending elastic modulus of 1 GPa or more and a thermal deformation temperature of 100° C. or higher,
- in which the polymethylpentene resin-containing material contains a polymethylpentene compound containing 1 to 300 ppm of a sulfur element based on mass.

<2>

The compression plate for a medical imaging apparatus according to <1>,

- in which a content of an olefin component other than a 4-methyl-1-pentene component in the polymethylpentene compound is 10 mol % or less.

<3>

The compression plate for a medical imaging apparatus according to <1> or <2>,

- in which the polymethylpentene compound contains 1 to 250 ppm of a sulfur element based on mass.

<4>

The compression plate for a medical imaging apparatus according to <1> or <2>,

- in which the polymethylpentene compound has a group represented by General Formula (1) at one terminal or both terminals, $$R\text{–}L\text{–}S^{*} \tag{1}$$

- in General Formula (1), R represents a hydrogen atom or a substituent, L represents a single bond or a linking group, and * represents a bonding site.

<5>

The compression plate for a medical imaging apparatus according to any one of <1> to < >4,

- in which a content of an ethylene-α-olefin copolymer in the polymethylpentene resin-containing material is 5% by mass or less,
- where, the ethylene-α-olefin copolymer does not contain a 4-methyl-1-pentene component.

<6>

The compression plate for a medical imaging apparatus according to <5>, in which an α-olefin component in the ethylene-α-olefin copolymer has 3 to 7 carbon atoms.

<7>

The compression plate for a medical imaging apparatus according to any one of <1> to <6>, in which the bending elastic modulus of the polymethylpentene resin-containing material is 1.4 GPa or more.

<8>

The compression plate for a medical imaging apparatus according to any one of <1> to <7>, in which the thermal deformation temperature of the polymethylpentene resin-containing material is 110° C. or higher.

<9>

A polymethylpentene resin-containing material for use in the compression plate for a medical imaging apparatus according to any one of <1> to <8>.

<10>

A medical imaging apparatus comprising:

a radiation generation unit;

a radiation detection unit;

an ultrasound probe;

an imaging table that is disposed between the radiation generation unit and the radiation detection unit; and a compression plate that compresses a subject by sandwiching the subject between the imaging table and the compression plate, in which the compression plate is the compression plate for a medical imaging apparatus according to any one of <1> to <8>.

The expression "to" in the present specification is used to mean that numerical values described before and after "to" are included as a lower limit value and an upper limit value.

In addition, in the present specification, in a case in which the number of carbon atoms in a certain group is defined, the number of carbon atoms means the number of carbon atoms of the group itself, unless otherwise specified in the present invention. That is, in a case in which the group is in a form further having a substituent (where, excluding a group in a form further having a substituent which can be construed as one group, such as a branched alkyl group), it means the number of carbon atoms counted without including the number of carbon atoms of the substituent.

The compression plate for a medical imaging apparatus according to an aspect of the present invention has excellent rigidity and is resistant to thermal deformation, abrasion, and yellowing. The polymethylpentene resin-containing material according to another aspect of the present invention can be suitably used for the compression plate for a medical imaging apparatus. The medical imaging apparatus according to still another aspect of the present invention has the compression plate for a medical imaging apparatus according to the aspect of the present invention.

BRIEF DESCRIPTION OF THE DRAWINGS

The FIGURE is a side view showing an imaging unit of one embodiment of a medical imaging apparatus according to the present invention.

DESCRIPTION OF THE PREFERRED EMBODIMENTS

<<Compression Plate for Medical Imaging Apparatus>>

A compression plate for a medical imaging apparatus according to an embodiment of the present invention (hereinafter, also simply referred to as a "compression plate according to the embodiment of the present invention") is used for a medical imaging apparatus including a radiation generation unit, a radiation detection unit, an ultrasound probe, and an imaging table disposed between the radiation generation unit and the radiation detection unit. The compression plate according to the embodiment of the present invention contains a polymethylpentene resin-containing material (a material containing a polymethylpentene resin) having a bending elastic modulus of 1 GPa or more and a thermal deformation temperature of 100° C. or greater, in which the polymethylpentene resin-containing material contains a polymethylpentene compound containing 1 to 300 ppm of a sulfur element based on mass.

The terms "radiation generation unit", "radiation detection unit", "ultrasound probe", and "imaging table" have the same meanings as the terms "radiation generation unit", "radiation detection unit", "ultrasound probe", and "imaging table" included in the medical imaging apparatus according to the embodiment of the present invention described below.

Both the "bending elastic modulus" and the "thermal deformation temperature" are values determined by a measuring method described in a section of Examples below.

The reason why the compression plate for a medical imaging apparatus according to the embodiment of the present invention has excellent rigidity and is resistant to thermal deformation, abrasion, and yellowing is not yet clear, but it is considered that this is because the polymethylpentene compound contained in the polymethylpentene resin-containing material contains a trace amount of sulfur element, so that oxidative degradation of the polymethylpentene resin-containing material is effectively suppressed, while conversely, the sulfur element itself is less likely to cause a reaction that degrades the polymethylpentene resin-containing material.

<Polymethylpentene Resin-Containing Material>

The compression plate according to the embodiment of the present invention contains a polymethylpentene resin-containing material, and the polymethylpentene resin-containing material contains a polymethylpentene compound.

The bending elastic modulus of the polymethylpentene resin-containing material used in the present invention is 1 GPa or more, and is preferably 1.4 GPa or more. On the other hand, the bending elastic modulus is practically 3 GPa or less, and is preferably 2 GPa or less.

The thermal deformation temperature of the polymethylpentene resin-containing material used in the present invention is 100° C. or higher, and is preferably 110° C. or higher and more preferably 120° C. or higher. On the other hand, the thermal deformation temperature is practically 160° C. or lower, and is preferably 140° C. or lower and more preferably 130° C. or lower.

The bending elastic modulus and the thermal deformation temperature of the polymethylpentene resin-containing material can be controlled by a content of a sulfur element in the polymethylpentene compound contained in the polymethylpentene resin-containing material, a weight-average molecular weight of the polymethylpentene compound, a type and a content of a copolymerization component other than methylpentene, and the like.

The polymethylpentene resin-containing material may be used alone or in combination of two or more kinds thereof.

The compression plate according to the embodiment of the present invention may contain a resin material other than the polymethylpentene resin-containing material having a bending elastic modulus of 1 GPa or more and a thermal deformation temperature of 100° C. or higher, within a range in which the effect of the present invention is not impaired. In the compression plate according to the embodiment of the present invention, a content of the polymethylpentene resin-containing material having a bending elastic modulus of 1 GPa or more and a thermal deformation temperature of 100° C. or higher can be, for example, 80% by mass or more, and is preferably 90% by mass or more and particularly preferably 100% by mass.

—Polymethylpentene Compound—

In the present invention, the term "polymethylpentene compound" means a homopolymer of 4-methyl-1-pentene and/or a copolymer of 4-methyl-1-pentene and an olefin other than 4-methyl-1-pentene. The bonding form of the copolymer is not particularly limited, and may be, for example, a block copolymer or a random copolymer.

Since it is possible to effectively increase the bending elastic modulus of the compression plate according to the embodiment of the present invention and to suppress the yellowing by rigidly maintaining a molecular structure of the polymethylpentene compound, a content of the olefin component other than the 4-methyl-1-pentene component in the polymethylpentene compound is preferably 10 mol % or less, more preferably 7 mol % or less, still more preferably 5 mol % or less, still more preferably 3 mol % or less, still more preferably 2 mol % or less, and still more preferably 1.5 mol % or less.

As the olefin component other than the 4-methyl-1-pentene component constituting the polymethylpentene compound, an α-olefin component is preferable, and the number of carbon atoms of the α-olefin is preferably 2 to 20 and more preferably 2 to 12.

Specific examples of the olefin from which the olefin component other than the 4-methyl-1-pentene component is derived include ethylene, propylene, 1-butene, 1-hexene, 1-octene, 1-decene, 1-tetradecene, and 1-octadecene. Among these, ethylene, propylene, 1-butene, 1-hexene, 1-octene, and 1-decene are preferred, ethylene, propylene, 1-butene, 1-hexene, and 1-octene are more preferred, ethylene, propylene, 1-butene, and 1-hexene are still more preferred, and propylene is particularly preferred.

The above-described olefin may be used alone or in combination of two or more kinds thereof.

The polymethylpentene compound used in the present invention contains, in a structure thereof, a sulfur element in an amount of 1 to 300 ppm based on mass, and preferably in an amount of 1 to 250 ppm, more preferably in an amount of 50 to 250 ppm, still more preferably in an amount of 100 to 250 ppm, still more preferably in an amount of 150 to 250 ppm, still more preferably in an amount of 160 to 220 ppm, and particularly preferably in an amount of 160 to 210 ppm.

In addition, it is also preferable to contain a sulfur element in an amount of 1 to 200 ppm, in an amount of 50 to 200 ppm, in an amount of 100 to 200 ppm, and in an amount of 150 to 200 ppm.

The polymethylpentene compound may have a sulfur element in any of a main chain, a side chain, or a terminal, and preferably has a sulfur element at the terminal. In a case in which polymethylpentene compound has a sulfur element at a terminal, the sulfur element may be provided at one terminal or both terminals.

It is preferable that the polymethylpentene compound has a group represented by General Formula (1) at one terminal or both terminals.

$$R\text{–}L\text{–}S^{*} \qquad (1)$$

In General Formula (1), R represents a hydrogen atom or a substituent, L represents a single bond or a linking group, and * represents a bonding site.

Examples of the substituent that can be adopted as R include an alkyl group, an aryl group, a hydroxy group, a carboxy group or a salt thereof, and a sulfo group or a salt thereof.

The aryl group preferably has 6 to 14 carbon atoms, and more preferably has 6 to 10 carbon atoms. Specific examples of the aryl group include phenyl and naphthyl.

The counter ions that can be adopted as the salt of the carboxy group and the salt of the sulfo group are not particularly limited, and examples thereof include sodium ions and potassium ions.

Examples of the linking group that can be adopted as L include an alkylene group, a carbonyl group, an ether bond, or a combination thereof, among these, an alkylene group is preferred.

The alkylene group may be linear, branched, or cyclic. The alkylene group preferably has 1 to 30 carbon atoms, and more preferably has 1 to 20 carbon atoms. Specific examples of the alkylene group include methylene, ethylene, propylene, 1-methylpropylene, 2-methylpropylene, butylene, pentylene, hexylene, cyclohexylene, heptylene, octylene, 2-ethylhexylene, decanylene, dodecylene, 1,1,2,2,3,3,4-heptamethylpentylene, tridecylene, hexadecylene, and octadecylene.

The alkylene group may have a substituent, and specific examples of the substituent include a hydroxy group and a carboxy group.

Specific examples of the above-described "combination thereof" include "alkylene group-carbonyl group-ether bond", "ether bond-carbonyl group-alkylene group", "alkylene group-carbonyl group-ether bond-alkylene group", "alkylene group-ether bond-carbonyl group-alkylene group", "alkylene group-carbonyl group", and "carbonyl group-alkylene group".

The group represented by General Formula (1) can be introduced into one terminal or both terminals of the polymethylpentene compound by using, for example, a compound represented by General Formula (2).

$$R\text{–}L\text{–}SH \qquad (2)$$

In General Formula (2), R and L have the same meanings as R and Lin General Formula (1), respectively, and preferred ranges are also the same.

Specific examples of the compound represented by General Formula (2) include 1-ethanethiol, 1-propanethiol, 1-butanethiol, 2-butanethiol, 2-methyl-1-propanethiol, 1-pentanethiol, 1-hexanethiol, cyclohexanethiol, 1-heptanethiol, 1-octanethiol, 1-decanethiol, 1-dodecanethiol, t-dodecanethiol (t-dodecylmercaptan), 1-hexadecanethiol, 1-octadecanethiol, mercaptoacetic acid, methyl mercaptoacetate, ethyl mercaptoacetate, 2-ethylhexyl mercaptoacetate, 3-mercaptopropionic acid, methyl 3-mercaptoacetate, n-hexyl 3-mercaptoacetate, cyclohexyl 3-mercaptoacetate, n-octyl 3-mercaptoacetate, 2-ethylhexyl 3-mercaptoacetate, dodecyl 3-mercaptoacetate, tridecyl 3-mercaptoacetate, hexadecyl 3-mercaptoacetate, octadecyl 3-mercaptoacetate, 2-mercaptoethanol, 3-mercapto-1,2-propanediol, sodium 2-mercaptoethanesulfonate, mercaptosuccinic acid, and thiophenol.

The polymethylpentene compound can be synthesized by a conventional method using a polymerization initiator as necessary, for example, with reference to JP2020-111731A and JP1999-335553A (JP-H11-335553A).

As the polymerization initiator, any of a photopolymerization initiator or a thermal polymerization initiator may be used, and for example, a polymerization initiator disclosed in WO2005/514559A and WO2005/103141A can be used.

The content of the sulfur element in the polymethylpentene compound can be controlled by a type and an amount of a chain transfer agent containing the monomer and the compound represented by General Formula (2), which are used for the synthesis.

A density ($g/cm^3$) of the polymethylpentene compound is not particularly limited, and is preferably 0.78 to 0.88 and more preferably 0.81 to 0.85.

The weight-average molecular weight of the polymethylpentene compound is not particularly limited, and is preferably 100000 to 1000000, more preferably 200000 to 800000, still more preferably 400000 to 600000, and particularly preferably 450000 to 530000.

The weight-average molecular weight of the polymethylpentene compound is a value determined by the following measuring method.

The measurement can be performed by gel permeation chromatography (GPC) using a differential refractive index (RI) detector with a GPC device HLC-8220 (trade name, manufactured by Tosoh Corporation) with o-dichlorobenzene used as an eluent and G3000HXL+G2000HXL (both are trade names, manufactured by Tosoh Corporation) as columns at 23° C. and a flow rate of 1 mL/min, and the weight-average molecular weight can be measured as a weight-average molecular weight in terms of polystyrene.

A content of the polymethylpentene compound in the polymethylpentene resin-containing material is preferably 95% by mass or more, more preferably 96% by mass or more, still more preferably 97% by mass or more, and particularly preferably 98% by mass or more, and may be 100% by mass.

The polymethylpentene resin-containing material used in the present invention preferably contains an ethylene-α-olefin copolymer. Note that the ethylene-α-olefin copolymer does not contain a 4-methyl-1-pentene component.

The polymethylpentene resin-containing material used in the present invention contains an ethylene-α-olefin copolymer, which imparts appropriate flexibility to the compression plate according to the embodiment of the present invention, prevents the bending elastic modulus from being excessively high, and makes a surface of the compression plate smooth, thereby effectively improving abrasion resistance.

—Ethylene-α-Olefin Copolymer—

The α-olefin contained in the ethylene-α-olefin copolymer is not particularly limited, and from the viewpoint of excellent abrasion resistance, an α-olefin having 2 to 10 carbon atoms is preferable, and an α-olefin having 2 to 6 carbon atoms is more preferable. The α-olefin may be linear, branched, or cyclic.

Specific examples of the α-olefin include propylene, 1-butene, 1-pentene, 1-hexene, 4-methyl-1-pentene, 1-octene, 1-decene, and cyclohexene, and among these, 1-butene, 1-hexene, and 1-octene are preferred.

A content of the α-olefin component in the ethylene-α-olefin copolymer is not particularly limited, and is preferably 1% to 49% by mass, more preferably 5% to 49% by mass, and still more preferably 10% to 49% by mass.

A density of the ethylene-α-olefin copolymer is not particularly limited, and is preferably 0.85 to 0.93 ($g/cm^3$) and more preferably 0.88 to 0.93 ($g/cm^3$).

A melt flow rate (MFR) of the ethylene-α-olefin copolymer is not particularly limited, and is preferably 0.5 to 50 g/10 min, more preferably 0.5 to 30 g/10 min, still more preferably 0.5 to 20 g/10 min, still more preferably 0.5 to 10 g/10 min, and particularly preferably 0.7 to 7.0 g/10 min.

The MFR of the ethylene-α-olefin copolymer is a value determined by the following measuring method.

Using a melt indexer ("Melt indexer G-02" manufactured by Toyo Seiki Seisaku-sho, Ltd.), the measurement is performed under conditions of a temperature of 190° C. and a load of 21.18 N according to Method A specified in JIS K7210-2 2014.

A weight-average molecular weight of the ethylene-α-olefin copolymer is not particularly limited, and is preferably 10000 to 300000, more preferably 50000 to 200000, still more preferably 60000 to 160000, and particularly preferably 70000 to 150000.

The weight-average molecular weight is a value determined by the following measuring method.

The measurement can be performed using a GPC device HLC-8121GPC/HT (trade name, manufactured by Tosoh Corporation) with 1,2,4-trichlorobenzene used as an eluent and TSKgel GMHhr-H (20) HT (trade name, manufactured by Tosoh Corporation) as a column at a column temperature of 140° C., and the weight-average molecular weight can be measured as a weight-average molecular weight in terms of polystyrene.

The ethylene-α-olefin copolymer can be synthesized by a conventional method. In addition, a commercially available product can also be used. Examples of the commercially available product include ENGAGE (registered trademark, manufactured by Dow Chemical Japan Ltd.), TAFMER (registered trademark, manufactured by Mitsui Chemicals, Inc.), NEO-ZEX and ULTZEX (both are registered trademarks, manufactured by Prime Polymer Co., Ltd.), and EXCELLEN, SUMIKATHENE, and ESPRENE (all are registered trademarks, manufactured by Sumitomo Chemical Co., Ltd.).

A content of the ethylene-α-olefin copolymer in the polymethylpentene resin-containing material can be, for example, 5% by mass or less, and is preferably 3% by mass or less and more preferably 2% by mass or less. On the other hand, the polymethylpentene resin-containing material may not contain the ethylene-α-olefin copolymer, or may contain 0.5% by mass or more thereof.

A proportion of the ethylene-α-olefin copolymer to the total content of the polymethylpentene compound and the ethylene-α-olefin copolymer in the polymethylpentene resin-containing material is preferably 0.2% to 5% by mass, more preferably 0.5% to 3% by mass, still more preferably 0.7% to 3% by mass, still more preferably 0.8% to 2.5% by mass, and particularly preferably 0.8% to 2.2% by mass.

From the viewpoint of improving transparency of the compression plate according to the embodiment of the present invention and the viewpoint of effectively suppressing scattering of ultrasonic waves, a degree of crystallinity of the polymethylpentene resin-containing material is preferably 20% or more, more preferably 22% or more, still more preferably 23% or more, still more preferably 24% or more, and still more preferably 25% or more. From the same viewpoint, the degree of crystallinity of the polymethylpentene resin-containing material is preferably 60% or less, more preferably 40% or less, still more preferably 35% or less, and also preferably 32% or less and further preferably 30% or less. In a case in which the degree of crystallinity of the polymethylpentene resin-containing material is preferably in a range of 20% to 60%, more preferably in 22% to 40%, still more preferably in a range of 22% to 35%, still more preferably in a range of 23% to 35%, still more preferably in a range of 23% to 32%, still more preferably in a range of 24% to 32%, and still more preferably in a range of 25% to 30%.

The degree of crystallinity is a value determined by the following calculation method.

Using a differential scanning calorimeter (manufactured by PerkinElmer, Inc., trade name: DSC-7), 10 mg of the polymethylpentene resin-containing material is held in a nitrogen atmosphere at 220° C. for 5 minutes and cooled to −40° C. at 10° C./min. A heat capacity of fusion ΔH is obtained from an area of a melting endothermic curveobtained by holding the sample at −40° C. for 5 minutes and heating the sample to 220° C. at 10° C./min, and the degree of crystallinity (%) is calculated using the following formula.

$$\text{Degree of crystallinity (\%)} = \Delta H/\Delta Hm0 \times 100$$

In the formula, ΔHmO represents a heat capacity of fusion of a perfect crystal, and is 100 J/g in poly(4-methyl-1-pentene).

The polymethylpentene resin-containing material used in the present invention may consist of a polymethylpentene compound or may consist of a polymethylpentene compound and an ethylene-α-olefin copolymer.

In addition, the polymethylpentene resin-containing material used in the present invention can appropriately contain an unreacted chain transfer agent, an antioxidant, a lubricant, a plasticizer, a light stabilizer, various fillers, and a colorant (for example, a pigment or a dye), in addition to the polymethylpentene compound and the ethylene-α-olefin copolymer, within a range in which the effect of the present invention is not impaired. In this case, a content of the component other than the polymethylpentene compound and other than the ethylene-α-olefin copolymer in the polymethylpentene resin-containing material used in the present invention is preferably 10% by mass or less, more preferably 8% by mass or less, still more preferably 6% by mass or less, still more preferably 4% by mass or less, particularly preferably 3% by mass or less, and also preferably 2% by mass or less.

<<Medical Imaging Apparatus>>

The medical imaging apparatus according to the embodiment of the present invention includes a radiation generation unit, a radiation detection unit, an ultrasound probe, an imaging table that is disposed between the radiation generation unit and the radiation detection unit, and a compression plate that compresses a subject by sandwiching the subject between the imaging table and the compression plate. As the compression plate, the compression plate for a medical imaging apparatus according to the embodiment of the present invention is used. At least a part of the imaging table need only be located on the radiation generation unit side with respect to the radiation detection unit.

In the medical imaging apparatus according to the embodiment of the present invention, X-rays are typically used as radiation, but α-rays, β-rays, γ-rays, electron beams, and the like can also be used.

The subject assumed by the medical imaging apparatus according to the embodiment of the present invention is typically a female breast, but the medical imaging apparatus according to the embodiment of the present invention can also use, for example, a finger, a hand, an arm, a leg, and an ankle as the subject.

In the medical imaging apparatus according to the embodiment of the present invention, the radiation generation unit generates radiation. The radiation detection unit detects the radiation emitted from the radiation generation unit and transmitted through the subject. The ultrasound probe moves along a surface of the compression plate according to the embodiment of the present invention on a side opposite to a surface in contact with the subject, and scans the subject with an ultrasonic wave to acquire an ultrasound image of the subject.

Specific examples of the medical imaging apparatus according to the embodiment of the present invention include a medical imaging apparatus in which the compression plate for a medical imaging apparatus according to the embodiment of the present invention is used as the first compression plate in the medical imaging apparatus disclosed in JP2009-82399A.

Hereinafter, one embodiment of the medical imaging apparatus according to the embodiment of the present invention will be described with reference to the drawings, but the present invention is not limited to the following embodiment except as specified in the present invention.

The FIGURE is a side view showing an appearance of an imaging unit of one embodiment of the medical imaging apparatus according to the present invention. As shown in the FIGURE, the imaging unit of the medical imaging apparatus includes an arm part 2, a base 3 that holds the arm part 2 movably in an up-down direction (Z axis direction), and a shaft part 4 that connects the arm part 2 to the base 3. The arm part 2 is provided with an X-ray tube 10, a filter 11, a radiation detection unit 12, an imaging table 19 disposed between the X-ray tube 10 and the radiation detection unit 12, a first compression plate 13 that compresses a subject 1 between a compression surface and a surface of the imaging table 19, a first compression plate moving mechanism 14 that moves the first compression plate 13 in the up-down direction (Z axis direction), an ultrasound probe 16 that acquires an ultrasound image of the subject by moving along an upper surface of the first compression plate 13 (a surface of the first compression plate on a side opposite to a surface in contact with the subject) on which echo jelly 24 is applied and scanning the subject with an ultrasonic wave, an ultrasound probe moving mechanism 17, a second compression plate 21 that compresses the echo jelly 24 with the first compression plate 13 to make a thickness of the echo jelly 24 uniform, and a second compression plate moving mechanism 22 that moves the second compression plate 21 in the up-down direction (Z axis direction).

The second compression plate is made of a polymethylpentene resin, a polycarbonate resin, an acrylic resin, or a polyethylene terephthalate resin.

Without being limited to the above-described apparatus configuration, for example, in apparatuses disclosed in JP6598721B, JP2009-082450A, JP2009-219656A, JP2020-162931A, and JP2020-162932A, the compression plate for a medical imaging apparatus according to the embodiment of the present invention can be used as a compression plate to form the medical imaging apparatus according to the embodiment of the present invention.

EXAMPLES

Hereinafter, the present invention will be described in more detail with reference to Examples. The present invention is not to be construed as being limited to the following examples except as specified in the present invention.

[Polymethylpentene Compound (Preparation of Component (A) in Table 1 Below)]

<Preparation of A-1>

With reference to JP2020-111731A, poly(4-methyl-1-pentene) [A-1 in Table 1 below, density: 0.833 g/cm$^3$, weight-average molecular weight: 497000, content of 4-methyl-1-pentene component in repeating unit composition of polymer: 100 mol %, sulfur element content: 180 ppm (based on mass)] was obtained using 4-methyl-1-pentene and t-dodecyl mercaptan.

The sulfur element content was measured and calculated by combustion ion chromatography. The same applies to the following sulfur element content.

<Preparation of A-2>

A propylene-4-methyl-1-pentene copolymer [A-2 in Table 1 below, density: 0.834 g/cm$^3$, weight-average molecular weight: 512000, content of propylene component in repeating unit composition of polymer: 3 mol %, content of 4-methyl-1-pentene component: 97 mol %, sulfur element content: 230 ppm (based on mass)] was obtained in the same manner as in the preparation of A-1, except that 4-methyl-1-pentene, propylene, and t-dodecyl mercaptan were used.

<Preparation of A-3>

A propylene-4-methyl-1-pentene copolymer [A-3 in Table 1 below, density: 0.835 g/cm$^3$, weight-average molecular weight: 528000, content of propylene component in repeating unit composition of polymer: 7 mol %, content of 4-methyl-1-pentene component: 93 mol %, sulfur element content: 270 ppm (based on mass)] was obtained in the same manner as in the preparation of A-2.

<Preparation of A-4>

A propylene-4-methyl-1-pentene copolymer [A-4 in Table 1 below, density: 0.837 g/cm$^3$, weight-average molecular weight: 536000, content of propylene component in repeating unit composition of polymer: 11 mol %, content of 4-methyl-1-pentene component: 89 mol %, sulfur element content: 310 ppm (based on mass)] was obtained in the same manner as in the preparation of A-2.

<Preparation of A-5>

A propylene-4-methyl-1-pentene copolymer [A-5 in Table 1 below, density: 0.838 g/cm$^3$, weight-average molecular weight: 541000, content of propylene component in repeating unit composition of polymer: 15 mol %, content of 4-methyl-1-pentene component: 85 mol %, sulfur element content: 340 ppm (based on mass)] was obtained in the same manner as in the preparation of A-2.

<Preparation of A-6>

Poly(4-methyl-1-pentene) [A-6 in Table 1 below, density: 0.833 g/cm$^3$, weight-average molecular weight: 463000, content of 4-methyl-1-pentene component in repeating unit composition of polymer: 100 mol %, sulfur element content: 280 ppm (based on mass)] was obtained in the same manner as in the preparation of A-1.

<Preparation of A-7>

Poly(4-methyl-1-pentene) [A-7 in Table 1 below, density: 0.833 g/cm$^3$, weight-average molecular weight: 412000, content of 4-methyl-1-pentene component in repeating unit composition of polymer: 100 mol %, sulfur element content: 410 ppm (based on mass)] was obtained in the same manner as in the preparation of A-1.

<Preparation of A-8>

Poly(4-methyl-1-pentene) [A-8 in Table 1 below, density: 0.833 g/cm$^3$, weight-average molecular weight: 365000, content of 4-methyl-1-pentene component in repeating unit composition of polymer: 100 mol %, sulfur element content: 590 ppm (based on mass)] was obtained in the same manner as in the preparation of A-1.

[Ethylene-α-Olefin Copolymer (Component (B) in Table 1 Below)]

The following ethylene-α-olefin copolymers were used as a component (B) in Table 1 below.

B-1: Ethylene-1-butene copolymer ("EXCELLEN VL102" (trade name), manufactured by Sumitomo Chemical Co., Ltd.), density: 0.91 g/cm$^3$, weight-average molecular weight: 121000, MFR: 0.9 g/10 min B-2: Ethylene-1-hexene copolymer ("EXCELLEN FX352" (trade name), manufactured by Sumitomo Chemical Co., Ltd.), density: 0.89 g/cm$^3$, weight-average molecular weight: 81000, MFR: 4.0 g/10 min

Examples 1 to 13 and Comparative Examples 1 to 10

A-1 prepared above as the component (A) was mixed with a Henschel mixer and melt-kneaded by a twin-screw extruder (manufactured by Nippon Steel Works, Ltd., "TEX-30αII" (trade name), barrel diameter: 30 mmq) at a set temperature of 280° C. to produce a pellet-shaped polymethylpentene resin-containing material (hereinafter, also referred to as a "resin pellet") of Example 1.

Resin pellets of Examples 2 to 4 and Comparative Examples 1 to 4 were produced in the same manner as in the production of the resin pellet of Example 1, except that the component (A) shown in Table 1 below was used.

Resin pellets of Examples 5 to 13 and Comparative Examples 5 to 10 were produced in the same manner as in the production of the resin pellet of Example 1, except that the components (A) and (B) shown in Table 1 below were used in the blending amounts shown in Table 1 below.

[Measurement of Bending Elastic Modulus]

A No. 1 dumbbell test piece was prepared from the above resin pellets by injection molding, and a bending elastic modulus of the test piece was measured by a bending test at 23° C. in accordance with JIS K7171 (2016) and evaluated according to the following evaluation standard.

<Evaluation Standard>

A: 1.4 GPa or more

B: 1.2 GPa or more and less than 1.4 GPa

C: 1 GPa or more and less than 1.2 GPa

D: less than 1 GPa

[Thermal Deformation Temperature]

A test piece having a length of 80 mm, a width of 10 mm, and a thickness of 4 mm was produced from the above resin pellets by injection molding. According to Method B specified in JIS K 7191-2 (2015), using an HDT test apparatus "3M-2 type" manufactured by Toyo Seiki Seisaku-sho, Ltd., a thermal deformation temperature of the test piece was obtained under conditions of a flat washer, a load of 0.45 MPa, and a temperature rising rate of 2° C./min, and heat resistance was evaluated according to the following evaluation standard.

<Evaluation Standard>

A: 120° C. or higher

B: 110° C. or higher and lower than 120° C.

C: 100° C. or higher and lower than 110° C.

D: lower than 100° C.

[Abrasion Resistance Test]

A hollow cylindrical test piece having an outer diameter of 25.6 mm, an inner diameter of 20 mm, and a length of 15 mm was produced from the above resin pellets by injection molding, and the amount of abrasion (mg) was measured by a ring abrasion test using a friction and abrasion tester "EFM-3 type" manufactured by A&D Co., Ltd. according to Method A (ring to ring) specified in JIS K7218 (1986). A ring (outer diameter: 25.6 mm, inner diameter: 20 mm, length: 15 mm) of S45C (carbon steel for a mechanical structure) was used as a mating material, and a test was performed under conditions of a speed of 30 m/min, a distance of 0.9 km, a load of 0.75 MPa, and a measurement environment temperature of 23° C., and the amount of abrasion was evaluated according to the following evaluation standard.

<Evaluation Standard>

A: The amount of abrasion was less than 30 mg.

B: The amount of abrasion was 30 mg or more and less than 100 mg.

C: The amount of abrasion was 100 mg or more and less than 200 mg.

D: The amount of abrasion was 200 mg or more.

[Yellowing Resistance Test]

A No. 1 dumbbell obtained in the same manner as the No. 1 dumbbell in the section of [Measurement of Bending Elastic Modulus] was placed in a heating oven set at 80° C. for 250 hours, and a color change before and after the heating was measured using a spectrometer ("MAX303" (trade name) manufactured by Asahi Spectra Co., Ltd.) in terms of a color difference ΔE* in accordance with JIS Z8730 (2009), and evaluated according to the following evaluation standard.

<Evaluation Standard>

A: ΔE* was less than 0.5.

B: ΔE* was 0.5 or more and less than 1.5.

C: ΔE* was 1.5 or more and less than 3.0.

D: ΔE* was 3.0 or more.

TABLE 1

| | | | Example 1 | Example 2 | Example 3 | Example 4 | Example 5 |
|---|---|---|---|---|---|---|---|
| Composition | Component (A) | Type | A-1 | A-2 | A-3 | A-6 | A-1 |
| | | Sulfur element content ppm (based on mass) | 180 | 230 | 170 | 280 | 180 |
| | | Content [% by mass] | 100.0 | 100.0 | 100.0 | 100.0 | 98.0 |
| | Component (B) | Type | — | — | — | — | B-1 |
| | | Content [% by mass] | | | | | 2.0 |
| Evaluation | Degree of crystallinity | | 28% | 26% | 21% | 20% | 26% |
| | Bending elastic modulus | [GPa] | A | B | C | A | A |
| | Thermal deformation temperature | [° C.] | A | A | B | C | A |
| | Abrasion resistance | | B | B | B | C | A |
| | Yellowing resistance | | A | B | C | C | B |

| | | | Example 6 | Example 7 | Example 8 | Example 9 | Example 10 |
|---|---|---|---|---|---|---|---|
| Composition | Component (A) | Type | A-2 | A-3 | A-1 | A-2 | A-3 |
| | | Sulfur element content ppm (based on mass) | 230 | 270 | 180 | 230 | 270 |
| | | Content [% by mass] | 98.0 | 98.0 | 98.0 | 98.0 | 98.0 |
| | Component (B) | Type | B-1 | B-1 | B-2 | B-2 | B-2 |
| | | Content [% by mass] | 2.0 | 2.0 | 2.0 | 2.0 | 2.0 |
| Evaluation | Degree of crystallinity | | 23% | 20% | 27% | 23% | 21% |
| | Bending elastic modulus | [GPa] | B | C | A | B | C |
| | Thermal deformation temperature | [° C.] | A | B | A | A | B |
| | Abrasion resistance | | A | A | A | A | A |
| | Yellowing resistance | | C | C | A | B | C |

| | | | Example 11 | Example 12 | Example 13 | Comparative Example 1 |
|---|---|---|---|---|---|---|
| Composition | Component (A) | Type | A-1 | A-1 | A-1 | A-4 |
| | | Sulfur element content ppm (based on mass) | 180 | 180 | 180 | 310 |
| | | Content [% by mass] | 99.0 | 97.0 | 96.0 | 100.0 |
| | Component (B) | Type | B-1 | B-2 | B-1 | — |
| | | Content [% by mass] | 1.0 | 3.0 | 4.0 | |
| Evaluation | Degree of crystallinity | | 27% | 24% | 20% | 16% |
| | Bending elastic modulus | [GPa] | A | B | B | D |
| | Thermal deformation temperature | [° C.] | A | A | B | D |

TABLE 1-continued

| | | | | | | |
|---|---|---|---|---|---|---|
| | | Abrasion resistance | A | B | C | D |
| | | Yellowing resistance | A | A | B | C |

| | | | Comparative Example 2 | Comparative Example 3 | Comparative Example 4 | Comparative Example 5 |
|---|---|---|---|---|---|---|
| Composition | Component (A) | Type | A-5 | A-7 | A-8 | A-1 |
| | | Sulfur element content ppm (based on mass) | 340 | 410 | 590 | 180 |
| | | Content [% by mass] | 100.0 | 100.0 | 100.0 | 94.0 |
| | Component (B) | Type | — | — | — | B-1 |
| | | Content [% by mass] | | | | 6.0 |
| Evaluation | Degree of crystallinity | | 7% | 16% | 13% | 10% |
| | Bending elastic modulus | [GPa] | D | B | B | D |
| | Thermal deformation temperature | [° C.] | D | D | D | D |
| | Abrasion resistance | | D | D | D | D |
| | Yellowing resistance | | D | D | D | C |

| | | | Comparative Example 6 | Comparative Example 7 | Comparative Example 8 |
|---|---|---|---|---|---|
| Composition | Component (A) | Type | A-1 | A-2 | A-2 |
| | | Sulfur element content ppm (based on mass) | 180 | 230 | 230 |
| | | Content [% by mass] | 94.0 | 94.0 | 94.0 |
| | Component (B) | Type | B-2 | B-1 | B-2 |
| | | Content [% by mass] | 6.0 | 6.0 | 6.0 |
| Evaluation | Degree of crystallinity | | 11% | 8% | 9% |
| | Bending elastic modulus | [GPa] | D | D | D |
| | Thermal deformation temperature | [° C.] | D | D | D |
| | Abrasion resistance | | D | D | D |
| | Yellowing resistance | | C | D | D |

| | | | Comparative Example 9 | Comparative Example 10 |
|---|---|---|---|---|
| Composition | Component (A) | Type | A-3 | A-3 |
| | | Sulfur element content ppm (based on mass) | 270 | 270 |
| | | Content [% by mass] | 94.0 | 94.0 |
| | Component (B) | Type | B-1 | B-2 |
| | | Content [% by mass] | 6.0 | 6.0 |
| Evaluation | Degree of crystallinity | | 7% | 8% |
| | Bending elastic modulus | [GPa] | D | D |
| | Thermal deformation temperature | [° C.] | D | D |
| | Abrasion resistance | | D | D |
| | Yellowing resistance | | D | D |

<Notes in Table>
"E": Example
"C": Comparative Example

The resin pellets of Comparative Example 1, which were produced using a polymethylpentene compound having a higher content of the sulfur element than the specified value of the present invention, had a lower bending elastic modulus and thermal deformation temperature than the specified values of the present invention, and as a result, the amount of abrasion was large. The resin pellets of Comparative Examples 2 to 4, which were prepared using a polymethylpentene compound having a higher content of the sulfur element, tended to have a higher bending elastic modulus than the resin pellets of Comparative Example 1, but the yellowing was more likely to occur.

The resin pellets of Comparative Examples 5 and 6, which were prepared using a polymethylpentene compound whose content of the sulfur element satisfied the specified value of the present invention and had a bending elastic modulus and a thermal deformation temperature not satisfying the specified value of the present invention, had a large amount of abrasion. In the resin pellets of Comparative Examples 7 to 10 in which the content of the sulfur element of the polymethylpentene compound was further increased in a state in which the resin pellets did not satisfy the bending elastic modulus and thermal deformation temperature specified in the present invention as in Comparative Examples 5 and 6, the yellowing was more likely to occur.

On the other hand, the polymethylpentene resin-containing material according to the embodiment of the present invention (resin pellets of Examples 1 to 13) had a sufficient bending elastic modulus and thermal deformation temperature, and was not only resistant to abrasion but also resistant to yellowing.

The present invention has been described using the embodiment. However, unless specified otherwise, any of the details of the above description is not intended to limit the present invention and can be construed in a broad sense within a range not departing from the concept and scope of the present invention disclosed in the accompanying claims.

EXPLANATION OF REFERENCES

1: subject
2: arm part
3: base
4: shaft part
10: X-ray tube
11: filter
12: radiation detection unit
13: first compression plate
14: first compression plate moving mechanism
16: ultrasound probe
17: ultrasound probe moving mechanism
19: imaging table
21: second compression plate
22: second compression plate moving mechanism
24: echo jelly

What is claimed is:

1. A compression plate for a medical imaging apparatus, which is used in a medical imaging apparatus including a radiation generation unit, a radiation detection unit, an ultrasound probe, and an imaging table disposed between the radiation generation unit and the radiation detection unit and which is used for compressing a subject by sandwiching the subject between the imaging table and the compression plate, the compression plate for a medical imaging apparatus comprising:

a polymethylpentene resin-containing material having a bending elastic modulus of 1 GPa or more and a thermal deformation temperature of 100° C. or higher, wherein the polymethylpentene resin-containing material contains a polymethylpentene compound containing 1 to 300 ppm of a sulfur element based on mass, and wherein the polymethylpentene compound has a group represented by Formula (1) at one terminal or both terminals, $$R\text{-}L\text{-}S^* \quad (1)$$

in Formula (1), R represents a hydrogen atom or a substituent, L represents a single bond or a linking group, and S* represents sulfur with a bonding site.

2. The compression plate for a medical imaging apparatus according to claim 1, wherein a content of an olefin component other than a 4-methyl-1-pentene component in the polymethylpentene compound is 10 mol % or less.

3. The compression plate for a medical imaging apparatus according to claim 1, wherein the polymethylpentene compound contains 1 to 250 ppm of a sulfur element based on mass.

4. The compression plate for a medical imaging apparatus according to claim 1, wherein a content of an ethylene-α-olefin copolymer in the polymethylpentene resin-containing material is 5% by mass or less, where, the ethylene-α-olefin copolymer does not contain a 4-methyl-1-pentene component.

5. The compression plate for a medical imaging apparatus according to claim 4, wherein an α-olefin component in the ethylene-α-olefin copolymer has 3 to 7 carbon atoms.

6. The compression plate for a medical imaging apparatus according to claim 1, wherein the bending elastic modulus of the polymethylpentene resin-containing material is 1.4 GPa or more.

7. The compression plate for a medical imaging apparatus according to claim 1, wherein the thermal deformation temperature of the polymethylpentene resin-containing material is 110° C. or higher.

8. A polymethylpentene resin-containing material for use in the compression plate for a medical imaging apparatus according to claim 1.

9. A medical imaging apparatus comprising:

a radiation generation unit;

a radiation detection unit;

an ultrasound probe;

an imaging table that is disposed between the radiation generation unit and the radiation detection unit; and a compression plate that compresses a subject by sandwiching the subject between the imaging table and the compression plate, wherein the compression plate is the compression plate for a medical imaging apparatus according to claim 1.

* * * * *